United States Patent [19]

Bertaux et al.

[11] 4,066,904
[45] Jan. 3, 1978

[54] METHOD OF MEASUREMENT OF THE CONCENTRATION OF A SUBSTANCE CONTAINED IN A GAS AND DEVICES FOR CARRYING OUT SAID METHOD

[75] Inventors: Jean-Loup Bertaux, Sevres; Jacques Alain Quessette, Paris, both of France

[73] Assignee: Agence Nationale de Valorisation de la Recherche Anvar, Neuilly-sur-Seine, France

[21] Appl. No.: 683,649

[22] Filed: May 6, 1976

[30] Foreign Application Priority Data

May 14, 1975    France .................................. 75.14952
Oct. 24, 1975    France .................................. 75.32644

[51] Int. Cl.$^2$ .......................................... G01N 21/22
[52] U.S. Cl. .................................. 250/372; 23/232 E; 250/373
[58] Field of Search .................... 250/423 P, 373, 372; 356/51; 23/232 E

[56] References Cited

U.S. PATENT DOCUMENTS

| | | | |
|---|---|---|---|
| 2,813,981 | 11/1957 | Friedman | 250/372 |
| 3,601,608 | 8/1971 | Randall et al. | 250/373 |
| 3,997,416 | 12/1976 | Confer | 25/232 E |

OTHER PUBLICATIONS

Davidson et al, "Direct Observation of the Rate of Recombination of Iodine Atoms," Journal of Chemical Physics, vol. 19, No. 10, p. 1311, Oct. 1951.
Baardsen et al, "Detection of OH in the Atmosphere Using a Dye Laser," Appl. Phys. Lett., vol. 21, No. 5, pp. 209–211, Sept. 1972.

Primary Examiner—Alfred E. Smith
Assistant Examiner—T. N. Grigsby
Attorney, Agent, or Firm—William R. Woodward

[57] ABSTRACT

In a method for measuring the concentration of a substance contained in a gas, the gas is irradiated with a radiation having a sufficiently short wavelength to photodissociate the substance. A photometric measurement is then carried out on at least one of the products of photodissociation in order to determine its concentration which is proportional to the concentration of the substance to be measured.

19 Claims, 5 Drawing Figures ately perform a quantitative analysis of a substance
METHOD OF MEASUREMENT OF THE CONCENTRATION OF A SUBSTANCE CONTAINED IN A GAS AND DEVICES FOR CARRYING OUT SAID METHOD

BACKGROUND OF THE INVENTION

This invention relates to a method of measurement of the concentration of a substance contained in a gas and to devices for carrying out said method. The invention finds an application especially in the measurement of the concentration of water vapor contained in a gas and in particular in the atmosphere. It can also apply to the detection of contaminants in the atmosphere.

When it is desired to measure the concentration of a substance contained in a gas, either the chemical or the physical properties of this substance are utilized in order to distinguish it from other substances which are present in the gas, a quantitative analysis of said substance being accordingly performed by means of these properties. It is thus a known practice to make use of optical methods based on measurement of the absorption exhibited by the substance to be determined at particular wavelengths or on the measurement of the luminescence which it exhibits under the action of various excitations.

All of these known methods are distinguished by the fact that the analysis is performed directly on the substance whose concentration is to be ascertained. In some instances, however, the physical or chemical characteristics of the substance having a concentration which it is desired to determine differ only to a slight extent from those of other substances which are present in the gas. This is the case, for example, of water vapor since the absorption spectrum exhibited by this latter cannot readily be differentiated from the spectra of other gases which are usually present in the atmosphere together with the water vapor. In this case the known methods are difficult to apply and are lacking in accuracy.

SUMMARY OF THE INVENTION

The invention has for its object a method which overcomes the aforementioned disadvantages insofar as it permits accurate and rapid measurement of the concentration of substances which do not have a clearly marked optical "signature". But the invention applies a fortiori to other substances for which the methods of the prior art would prove suitable.

The method according to the present invention essentially consists first in carying out a photodissociation of the substance whose concentration is to be measured, then in carrying out a photometric measurement on at least one of the products of photodissociation and not on the original substance as in the prior art. Thus, when the substance whose concentration is to be measured is water vapor, the water molecule is photodissociated, thereby producing a hydrogen atom and an OH radical. Photometric measurements are then taken in order to determine the concentration either of hydrogen atoms or of OH radicals, this concentration being proportional to the water vapor concentration prior to dissociation.

The advantage of this method lies in the fact that, as stated earlier, it may prove much easier to perform the photometric measurements on the products of dissociation than on the substance to be determined since, in the case of water vapor for example, the optical signature of both the hydrogen atom and the OH radical is very characteristic.

The photometric measurement which is taken after photodissociation can assume a number of different forms. When the radiation which is employed in order to irradiate the gas and to induce photodissociation has a sufficiently short wavelength to ensure that at least one of the products of dissociation is created in an excited state, the photometric measurement can consist of a measurement of intensity of the light emitted at the time of de-excitation of the excited product. But when the products of dissociation are created in a non-excited state, the photometric measurement can consist of a measurement of absorption or of a measurement of fluorescence if recourse is had to a second radiation which is capable of inducing said fluorescence.

In the case of application to the measurement of the concentration of water vapor in a gas, the first alternative embodiment of the method is obtained when the wavelength of the radiation employed in the irradiation process is shorter than 1360 A, the OH radical being produced in that case in an excited state; de-excitation of this radical causes the emission of radiation within the range of 3000 to 3250 A. But the photometric measurement can also be carried out on hydrogen, in which case it takes place at 1216 A on the so-called Lyman alpha resonance line.

The invention also has for its object a device for carrying out the method which has just been defined. Said device is characterized by the existence of a source of radiation having a wavelength which is sufficiently short to photodissociate the substance whose concentration is to be measured and by photometric measuring means which are capable of determining the concentration of at least one of the photodissociation products.

In the application to measurement of the concentration of water vapor, the device comprises a source which emits a radiation having a wavelength of less than 1360 A and measuring means constituted by a photodetector having a range of sensitivity which contains the waveband from 3000 to 3250 A.

In one particular embodiment, the source emits radiation at 1216 A which corresponds to the Lyman alpha resonance line of hydrogen.

BRIEF DESCRIPTION OF THE DRAWINGS

The characteristic features and advantages of the invention will in any case become more readily apparent from the following description of exemplified embodiments which are given by way of explanation and not in any limiting sense, reference being had to the accompanying drawings, in which.

DESCRIPTION OF THE PREFERRED EMBODIMENTS

In order to simplify the following description, it will be assumed solely by way of explanation that the substance whose concentration is to be determined is water vapor. It remains apparent, however, that there would not be any departure from the scope of the invention if the method and devices described hereinafter were applied to substances other than water vapor since, as has already been pointed out, the invention applies to the measurement of the concentration of any substance contained in a gas.

The water molecules contained in a gas dissociate when they absorb photons of sufficiently high energy. In particular, irradiation with photons having energies higher than 9.25 eV corresponding to a wavelength below 1360 A gives rise to excitation of the water molecule followed by dissociation of this latter into a hydrogen atom and an OH radical. When the energy of the irradiation photons is of sufficiently high value, the OH radical can be produced in an excited state. At the time of de-excitation, the radical emits a photon having a wavelength within the range of about 3000 A to 3250 A. In order to excite the hydrogen atom, it is possible to employ photons having a wavelength of 1216 A which are adapted to the resonance line of atomic hydrogen, known as the Lyman alpha line. This line is intense and relatively narrow ($10^{-1}$ A).

Figure 1:
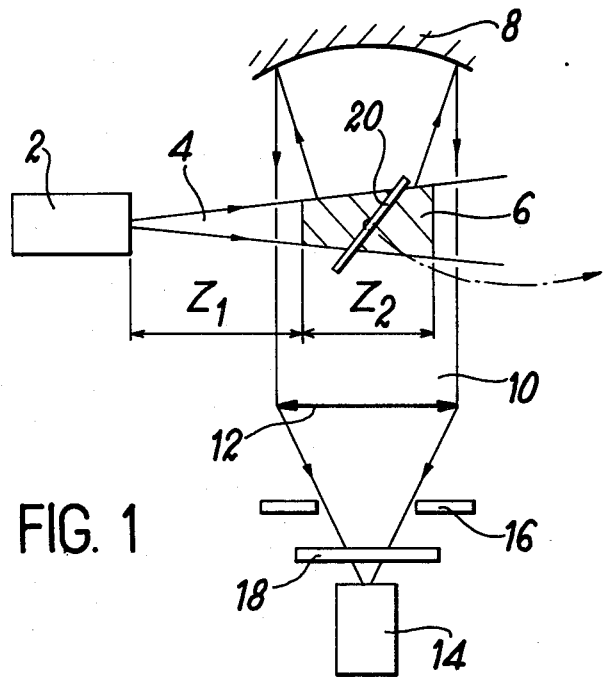
FIG. 1 is a schematic illustration of a first embodiment of the device in which a local measurement is carried out on the intensity emitted at the time of deexcitation of one of the dissociation products.

The device which is illustrated diagrammatically in FIG. 1 serves to carry out a photometric measurement on the excited OH radicals. The device shown comprises a light source 2 which emits a light beam 4 containing photons having a wavelength which is shorter than 1360 A and therefore lie in the far-ultraviolet region of the spectrum. This light beam is directed onto the gas to be studied and the common zone of the beam 4 and of the gas defines an interaction space 6. The photons emitted by the source 2 dissociate the water molecules contained in the space 6. Since the energy of the radiation employed in the irradiation process is sufficient to produce the OH radical in an excited state, there is produced within the space 6 a stream of photons having wavelengths ranging approximately from 3000 to 3250 A. A photodetector 14 having a range of sensitivity which includes the range of 3000 to 3250 A receives part of the de-excitation radiation and the signal delivered by said photodetector reflects the concentration of OH radicals and consequently the concentration of water vapor which is proportional thereto.

If so required, a mirror 8, a lens 12 and a diaphragm 16 can complete the device. If necessary, an optical system 18 which transmits only photons having a wavelength within the range of emission of the OH* radicals can be placed in front of the photodetector 14. Said means 18 are advantageously constituted by an interference filter or a diffraction grating which is centered approximately on 3100 A.

As will be explained hereinafter, it is useful to determine the intensity of the incident radiation which arrives within the excited space. To this end, said intensity can be measured directly at the exit of the source 2 but, in an advantageous embodiment, said measurement is carried out directly in the zone 6 by placing a retractable scintillator 20 within the zone 6. Said scintillator converts the far-ultraviolet photons emitted by the source 2 to photons having a wavelength which falls within the range of sensitivity of the detector 14. By way of example, said scintillator can be constituted by a layer of sodium salicyalate. In particular, a substance of this type converts the photons at 1216 A corresponding to the Lyman alpha resonance line to a wavelength in the vicinity of 3000 A.

In order that the principle of operation of the apparatus which is illustrated in FIG. 1 may be more clearly understood, a few theoretical considerations can accordingly be given. It should be clearly understood that these considerations are given solely by way of explanation and that the scope of the patent is in no way dependent on their exactitude or on the validity of the simplifying assumptions on which they are based.

In the following description, $Z_1$ designates the path followed by the photons emitted by the source 2 prior to arrival of said photons within the space 6, $Z_2$ designates the length of the space 6 and $\tau$ designates the optical thickness in water. The optical thickness $\tau$ of a substance is defined by the following relation:

$$\tau = \sigma n Z \qquad (1)$$

wherein $\rho$ represents the cross-section for absorption of photons by the substance considered, $n$ represents the number of molecules per cm$^3$ of the substance and $Z$ represents the length of the interaction space.

The intensity I emitted by the OH* radicals which are de-excited is given by the relation:

$$I = \alpha I_O e^{-\tau_1}(1 - e^{-\tau_2}) \qquad (2)$$

in which $\alpha$ represents the optical efficiency of the apparatus, $I_O$ represents the intensity of the light beam 4 emitted by the source 2, $\tau_1$ and $\tau_2$ represents the optical thicknesses in water respectively in the case of the lengths $Z_1$ and $Z_2$.

The coefficient $\alpha$ is dependent on the efficiency of dissociation of the water molecules by the photons, on the optical transmission of the medium $e$, on the number of impact de-excitations of the OH* radicals (the so-called quenching phenomenon). In the case of a given apparatus, this coefficient is measured once and for all by calibration.

In relation (2), the term $I_O e^{-\tau_1}$ represents the number of photons which penetrate into the space 6 after a transition through a length $Z_1$. The term $(1-e^{-\tau_2})$ is the number of photons absorbed within the space 6 and the number of photons re-emitted by the OH* radicals is proportional thereto.

If a scintillator 20 is placed within the space 6, which converts the wavelength of the beam 4 to a wavelength to which the photodetector 14 is sensitive, there is obtained a scattered beam having an intensity which is given by the relation:

$$I_D = I_O e^{-\tau_1} \qquad (3)$$

As a result of relations (2) and (3), we may write:

$$I/I_D = \alpha(1 - e^{-\tau_2})$$

and, if $\tau_2$ is of small value,:

$$I/I_D = \alpha \tau_2$$

a knowledge of the ratio $I/I_D$ makes it possible to calculate $\tau_2$ if the value of $\alpha$ is known, which can be obtained by calibration. From a knowledge of the value of the cross-section $\rho$, the value of $\alpha$ and $Z_2$, it is possible to deduce by means of relation (1) the value of $n$ which is the number initially sought of water molecules per cm$^3$ contained within the space 6.

It is readily apparent that the determination of the intensity $I_D$ by means of the scintillator 20 can be performed once and for all in respect of different measurements of concentration. The use of a scintillator can even be avoided by adopting an apparatus as shown in FIG. 2 which is no longer based on a local measurement but on two measurements taken simultaneously in two different zones of the gas space to be studied.

Figure 2:
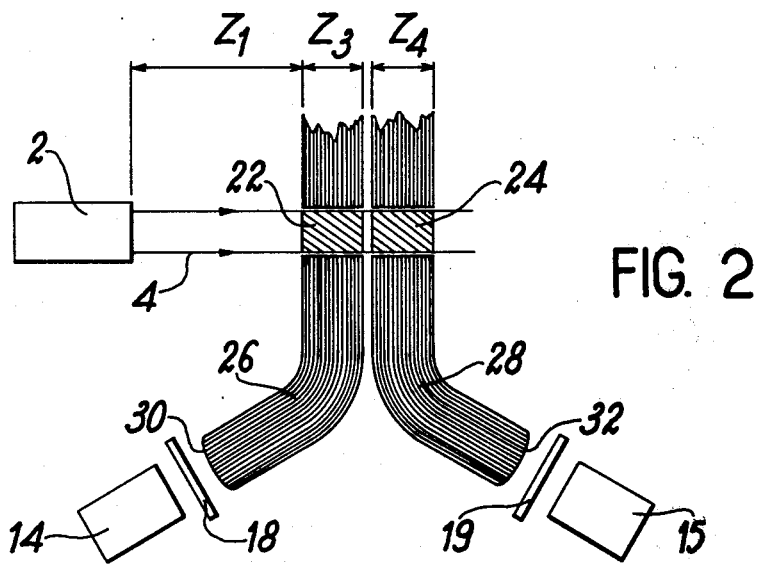
FIG. 2 illustrates an alternative embodiment of the device in which two measurements of intensity are carried out simultaneously in two different zones of the gas.

The apparatus which is illustrated in FIG. 2 is preferably employed for the determination of water vapor concentrations such that the optical thickness in water in respect of a length of approximately 0.5 cm is within the range of 0.05 to 2.5. In this apparatus, there is again shown a light source 2 which emits far-ultraviolet photons in the form of a light beam 4. Photometric measurement is carried out in a first zone 22 and in a zone 24. Optical means constituted for example by optical fibers 26 and 28 are placed opposite to the zones 22 and 24 in order to guide the light emitted in these zones onto the photodetectors 14 and 15. The ends 30 and 32 of the bundle of optical fibers can be optically cut if necessary so that they may be permitted to perform the function of convergent lenses. Optical systems 18 and 19 placed between the ends 30 and 32 of the optical fibers and the photodetectors 14 and 15 transmit only those photons which have a wavelength within the range of emission of the OH* radicals, that is, within the range of about 3000 to 3250 A. There are thus provided two simultaneous measurement channels, each channel being associated with an interaction space.

The principle of the measurement is as follows: each photodetector 14 or 15 measures the intensity of the light transmitted by the optical means 26 or 28 and the systems 18 or 19. This light is derived from the de-excitation of the OH* radicals which are present within the zones 22 or 24.

In the description given hereinafter, the reference $Z_1$ designates the distance between the source and the zone 22, the reference $Z_3$ designates the length of the zone 22 and the reference $Z_4$ designates the length of the zone 24. The references $\tau_1$, $\tau_3$ and $\tau_4$ designate the optical thicknesses in water on the paths having the respective lengths $Z_1$, $Z_3$ and $Z_4$ and the reference $I_0$ designates the intensity of the light beam 4 emitted by the source 2. The number of photons which arrive within the zone 22 is equal to $I_0 e^{31}\tau_1$. Assuming by way of example and in order to simplify the following explanation that the zones 22 and 24 have the same length ($Z_3 = Z_4$), the optical thicknesses in water $\tau_3$ and $\tau_4$ are equal and the light intensity $I_3$ detected by the photodetector 14 associated with the zone 22 is given by the following relation:

$$I_3 = \alpha_3 I_0 e^{-\tau_1}(1 - e^{-\tau_3}) \qquad (4)$$

Similarly, the light intensity $I_4$ detected by the photodetector 15 associated with the zone 24 is given by the relaion:

$$I_4 = \alpha_4 I_0 e^{-\tau_1} e^{-\tau_3}(1 - e^{-\tau_3}) \qquad (5)$$

In this relation (5) which is valid only in respect of $Z_3 = Z_4$, the term $\alpha_4 I_0 e^{-\tau_1} e^{-\tau_3}$ corresponds to the number of photons which arrive within the second zone 24. From relations (4) and (5), there is immediately derived:

$$I_3/I_4 = (\alpha_3/\alpha_4)e^{-\tau_3} \qquad (6)$$

When the values of $\tau_3$ are of a low order, relation (6) may be written:

$$I_3/I_4 = (\alpha_3/\alpha_4)(1 - \tau_3) \qquad (7)$$

The values of $\alpha_3$ and $\alpha_4$ being determined by calibration of the apparatus, relation (6) (or relation (7)) and relation (1) make it possible to calculate the number of water molcules per cm$^3$ which are contained within the zones 22 and 24.

It is self-evident that the simultaneous character of the measurements performed within the two zones 22 and 24 is not necessary. It would be entirely feasible to employ a single detector which first scans the zone 22 then scans the zone 24 provided of course that the result of the measurement relating to the zone 22 is stored in memory in order to permit the possibility of combining this latter with the result obtained subsequently in respect of the zone 24.

Figure 3:
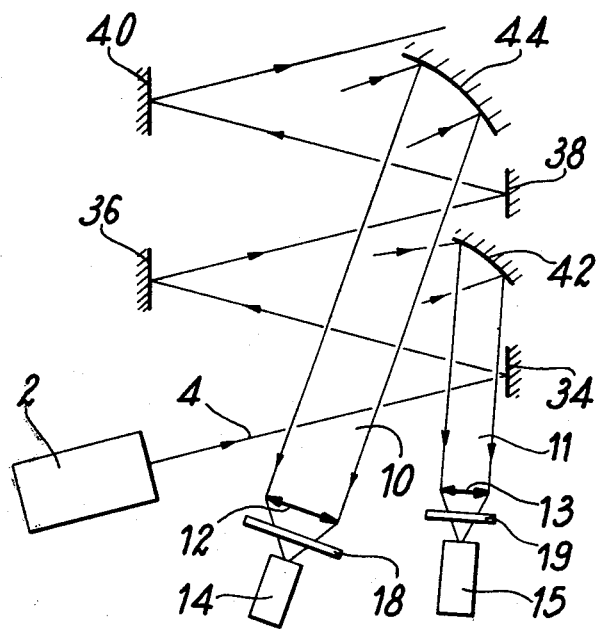
FIG. 3 illustrates another alternative embodiment of the device in which the length of the path of the incident radiation is increased by the action of a set of mirrors.

The apparatus which is shown diagrammatically in FIG. 3 is advantageously employed in the case of a dry gas, the optical thickness in water of said gas being approximately within the range of $10^{-3}$ to $10^{-2}$ for a distance of travel of 1 cm. In this alternative embodiment of the invention, the light beam 4 delivered by the light source 2 passes through the gas to be studied a number of times. A greater interaction length is thus made available. This result is obtained by means of the set of mirrors 34, 36, 38 and 40 which are placed in the gas to be studied and from which the light beam 4 is reflected.

Mirrors 42 and 44, especially of the spherical type, are placed at a certain distance from each other in the gas under study. These mirrors which reflect the light emitted during de-excitation of the OH* radicals determine two interaction spaces as in the hygrometer shown in FIG. 2. A fraction of the photons emitted by the OH* radicals which are de-excited is reflected from the mirrors 42 and 44 in the form of beams 10 and 11 towards the photodetectors 14 and 15. Said photodetectors are associated with convergent lenses 12 and 13 and with selective optical systems 18 and 19 which transmit only those photons having a wavelength which lies within the emission band of the OH* radicals.

In this alternative embodiment as in that of FIG. 2, there therefore appear two measuring channels which serve to determine simultaneously the light intensity emitted by the OH* radicals. The use of mirrors instead of optical fibers (as in the alternative embodiment of FIG. 2) permits a considerable increase in the space provided for interaction of the photons emitted by the light source with the water molecules and is therefore conductive to higher sensitivity of measurement.

A knowlege of the intensities $I_3$ and $I_4$ detected by the photodetectors 14 and 15 makes it possible as in the case of the hygrometer shown in FIG. 2 to determine the number of water molecules per cm$^3$ contained in the gas to be studied by means of relations (1) and (7). By way of example, the length over which the light beam 4 is caused to interact with the gas to be studied can attain several meters.

Figure 4:
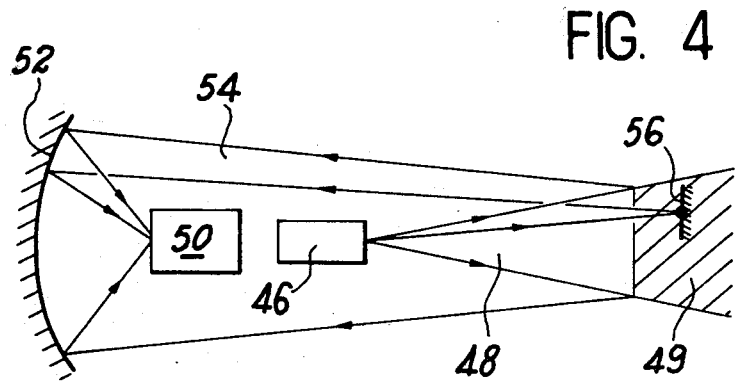
FIG. 4 is a schematic illustration of another alternative embodiment which is adapted to a photometric measurement by resonance on hydrogen atoms.

In the hygrometer which is shown diagrammatically in FIG. 4, the emission of the OH* radicals is no longer employed as in the previous examples of application but is replaced by the resonance of the hydrogen atoms formed at the time of photodissociation of the water molecules. This resonance takes place at 1216 A in the case of the Lyman alpha line. This alternative mode of execution is advantageously employed for measuring the concentration of water in very dry air at low pressure within a vacuum chamber or at high altitude, for example. This method is even more advantageous by virtue of the fact that oxygen presents a transmission window at the wavelength of the Lyman alpha line.

The hygrometer which is represented schematically in FIG. 4 comprises a light source 46 for emitting photons having a wavelength of 1216 A. Said light source is, for example, a hydrogen source which emits photons corresponding to the Lyman alpha line. The beam 48 emitted by the source 46 interacts with the gas to be studied within a zone 49. Under the action of the photons of the light source, the water molecules are dissociated into hydrogen atoms and into OH radicals and the incident photons give rise simultaneously to resonance of the hydrogen atoms derived from the dissociation of the water molecules. Photons are therefore re-emitted at 1216 A and are detected by the photodetector 50 which may be associated if necessary with a spherical mirror 52.

As in the case of the alternative embodiment illustrated in FIG. 1, means can be provided for measuring the intensity $I_O$ of the radiation emitted by the light source 46. To this end, a retractable mirror 56 treated for reflecting photons at 1216 A can be placed on the path of the light beam 48. Said mirror 56 reflects the photons emitted by the source 46 towards the mirror 52 then towards the photodetector 50. The measurement of the intensity $I_O$, the determination of the intensity of the photons re-emitted by the hydrogen atoms, the knowledge of the values of the absorption cross-sections of hydrogen and of water, make it possible to determine as in the alternative embodiment of FIG. 1, the number of hydrogen atoms which ae present within the zone 49 and consequently the number of water vapor molecules which is proportional thereto.

The disadvantage of this embodiment lies in the fact that the photodissociation radiation takes place at the same wavelength as the radiation on which the photometric measurement takes place (1216 A). It may be preferable in some cases to work with radiations having two different wavelengths, one radiation being intended to photodissociate the substance whose concentration is to be measured whilst the other radiation serves to carry out the photometric measurement.

Figure 5:
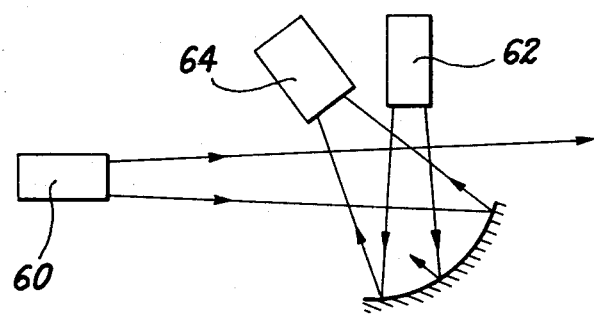
FIG. 5 is a schematic illustration of an alternative embodiment which makes use of a measurement of fluorescence.

Thus, in accordance with the arrangement illustrated in FIG. 5, it is possible to employ a first light source 60 which emits a radiation at 1600 A, thus permitting photodissociation of the water without thereby procuding OH radicals in an excited state and a second source 62 which emits at 1216 A, which makes it possible to determine the number of hydrogen atoms by means of the resonance on the Lyman alpha line. The intensity of the re-emitted radiation is measured by means of a photodetector 64 which is sensitive at 1216 A. In this manner, the problems of extraneous light which are liable to arise in the embodiment of FIG. 4 are accordingly avoided.

In all the examples described in the foregoing, the photodetectors can be photomultipliers; the sources can in some cases be lasers.

We claim:

1. A method of measurement of the concentration of a photodissociable substance contained in a gas, wherein:
    a gas having an unknown content of photodissociable substance is irradiated with a radiation having a sufficiently short wavelength to photodissociate said substance,
    a photometric measurement is carried out on at least one of the photodissociation products in order to determine its concentration under conditions under which the concentration of the photodissociation product is proportional to the concentration of the substance to be measured.

2. A method according to claim 1, wherein the dissociation products are produced in a non-excited state, and said photometric measurement consists of a measurement of absorption.

3. A method according to claim 1, wherein the dissociation products are produced in a non-excited state, and said photometric measurement consists of a measurement of fluorescence.

4. A method according to claim 1, and wherein said substance is water vapor, the dissociation products are the hydrogen atom H and the OH radical.

5. A method according to claim 1, wherein the radiation with which said gas is irradiated has a sufficiently short wavelength to ensure that at least one of the photodissociation products is created in an excited state, whereupon said photometric measurement consists in measuring the intensity of the light emitted at the time of de-excitation of said excited product.

6. A method according to claim 5, wherein said substance is water vapor, the dissociation products being the hydrogen atom H and the OH radical, and wherein the wavelength of the radiation employed in the irradiation step is 1216 A corresponding to the Lyman alpha line of hydrogen.

7. A method according to claim 6, wherein the photometric measurement takes place on the optical resonance of hydrogen at 1216 A.

8. A method of measurement of the concentration of water vapor contained in a gas, wherein:
    said gas is irradiated with a radiation having a sufficiently short wavelength shorter than 1360 A to dissociate the water vapor into dissociation products consisting of the hydrogen atom H and the OH radical, the latter being accordingly produced at the time of photodissociation in an excited OH* state, and
    photometric measurement is carried out which consists in measuring the intensity of the radiation emitted within the range of 3000 to 3250 A at the time of de-excitation of the OH* radical.

9. A method of measurement of the concentration of a substance contained in a gas, wherein:
    a gas having an unknown content of a photodissociable substance is irradiated with a radiation having a sufficiently short wavelength to photodissociate said substance,
    a photometric measurement is carried out in two different zones of the gas on at least one of the photodissociation products in order to determine its concentration under conditions under which the concentration of the photodissociation product is proportional to the concentration of the substance to be measured, and a comparison of the results obtained in respect of the two zones is performed to determine the concentration of said substance.

10. A device for measuring the concentration of a photodissociable substance contained in a gas, which device comprises:

a source of radiation which emits a radiation having a wavelength shorter than 1360 A disposed for irradiating a volume of said gas, and photometric measuring means constituted by at least one photodetector having a range of sensitivity which includes the waveband from 3000 A to 3250 A, disposed for detecting emission of said radiation in said gas.

11. A device according to claim 10, wherein said device comprises a single measuring channel constituted by a photodetector mounted on orientable mechanical means for scanning a number of zones of the gas.

12. A device according to claim 10, wherein said device further comprises a retractable scintillator which is placed in that zone of the gas in which the measurement is carried out and converts the radiation employed in the irradiation process to a radiation having a wavelength which falls within the range of sensitivity of the photodetector.

13. A device according to claim 12, wherein the retractable scintillator is of sodium salicylate.

14. A device according to claim 10, wherein said device comprises two measuring channels each constituted by a photodetector having a range of sensitivity which contains the waveband from 3000 to 3250 A, said channels being intended to measure the radiation issuing from two separate zones of the gas which are traversed successively by the radiation emitted by the source.

15. A device according to claim 14, wherein each channel further comprises a bundle of optical fibers placed between the gas zone under study and the photodetector.

16. A device according to claim 10 for measuring the concentration of water vapor in a gas, wherein the source emits radiation in which the spectrum contains the wavelength of 1216 A.

17. A device according to claim 16, wherein said device comprises at least one photodetector which is sensitive at 1216 A.

18. A device for measuring the concentration of a photodissociable substance in a gas, which device comprises:

a first source of radiation having a wavelength shorter than 1360 A for irradiating the gas, and photometric measuring means constituted by a second radiation source in which the spectrum contains the wavelength of 1216 A and by a photodetector which is sensitive at 1216 A.

19. A method of measuring the concentration of contaminants in the atmosphere, wherein:

a volume of atmospheric air is irradiated with a radiation having a sufficient short wavelength to photodissociate contaminants, a photometric measurement is carried out in two different zones of the irradiated air on at least one of the photodissociation products in order to determine its concentration under conditions under which the concentration of the photodissociation product is proportional to the concentration of a contaminant of which it is a photodissociation product, and a comparison of the results obtained in respect of the two zones is performed to determine the concentration of said contaminant.

* * * * *